United States Patent [19]

Sato et al.

[11] 4,198,312
[45] Apr. 15, 1980

[54] 3'-CHLORO-4'-CYANOPHENYL 4-N-ALKYLBENZOATES

[75] Inventors: Hisato Sato, Tabata; Haruyoshi Takatsu, Kodaira; Yutaka Fujita, Yokohama, all of Japan

[73] Assignees: Dainippon Inc. & Chemicals, Inc.; Hitachi, Ltd., both of Tokyo, Japan

[21] Appl. No.: 959,441

[22] Filed: Nov. 13, 1978

[30] Foreign Application Priority Data

Nov. 18, 1977 [JP] Japan .................. 52-138480

[51] Int. Cl.² .............. C07C 121/60; C09K 3/34; G02F 1/13
[52] U.S. Cl. .................. 252/299; 260/465 D; 350/350
[58] Field of Search .............. 260/465 D; 252/299

[56] References Cited

U.S. PATENT DOCUMENTS 3,923,857  12/1975  Boller et al. .............. 260/465 D
4,110,243   8/1978  Abert-Mellah et al. ........ 252/299

Primary Examiner—Dolph H. Torrence
Attorney, Agent, or Firm—Sherman & Shalloway

[57] ABSTRACT

Novel compounds of the formula

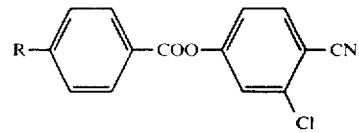

wherein R represents a linear alkyl group containing 1 to 9 carbon atoms. When added to nematic liquid crystals for electro-optical display elements, these compounds enable the liquid crystals to be operated at low voltages.

13 Claims, 1 Drawing Figure

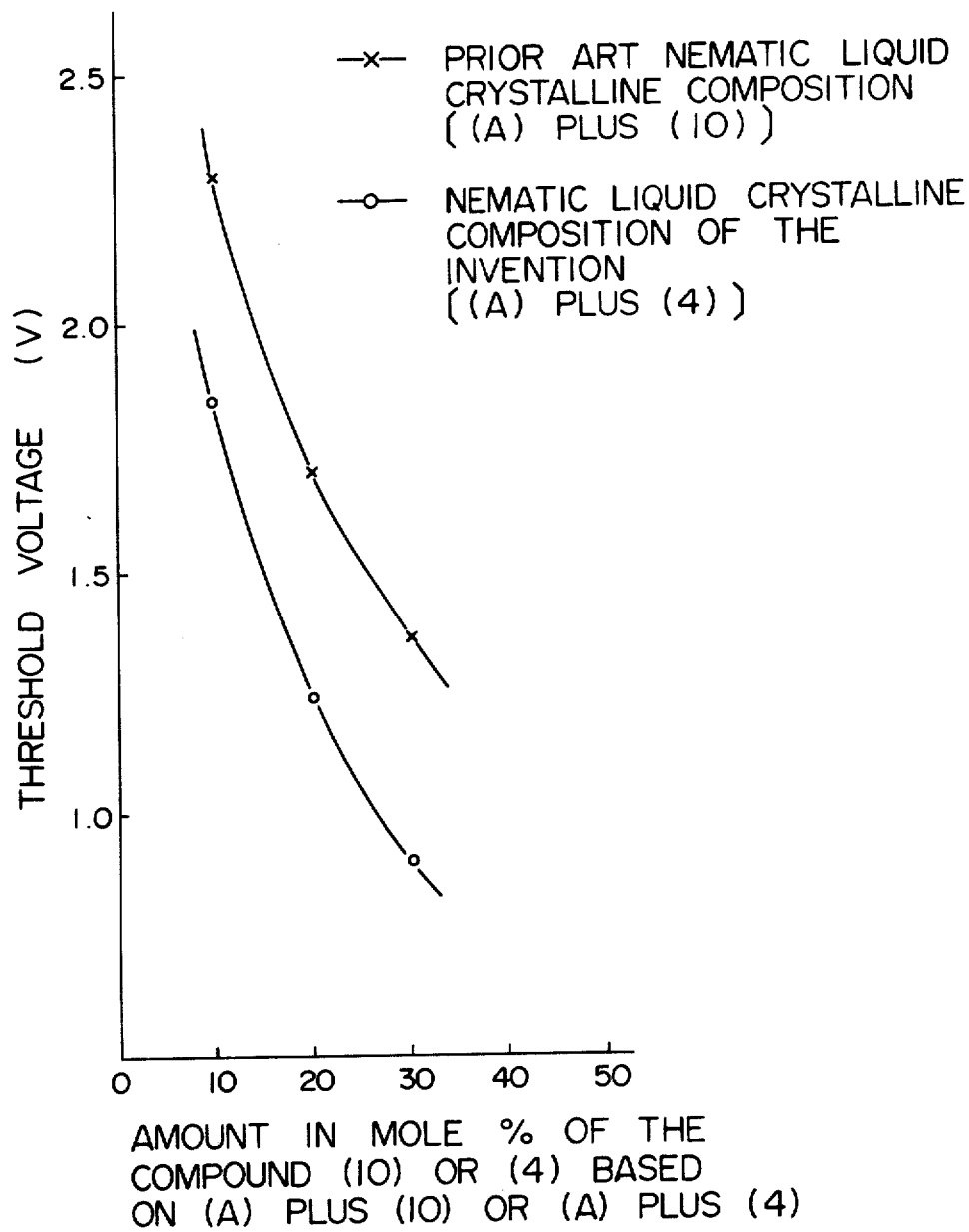

3'-CHLORO-4'-CYANOPHENYL 4-n-ALKYLBENZOATES

This invention relates to novel compounds which when added to nematic liquid crystals for electro-optical display elements, enable the liquid crystals to be operated at low voltages.

One typical liquid crystal display cell is the field effect mode (F.E.M.) cell suggested by M. Schadt et al. [APPLIED PHYSICS LETTERS, 18, 127–128 (1971)]. The F.E.M. cell consists of two transparent electrode plates disposed parallel to each other and nematic liquid crystals having positive dielectric anisotropy filled between the electrode plates. The liquid crystal molecules form a helical arrangement twisted at a certain angle between the electrode plates, and therefore, have a certain ability to polarize the incident light. When a voltage is applied across the electrode plates, the liquid crystal molecules are aligned with their long axes being perpendicular to the electrode plates, and therefore, their polarizing ability disappears. By using a polarizing plate, the variations in polarizing ability are converted to variations in optical transmittance of the cell, thus permitting display. Nematic liquid crystals used in F.E.M. cells should have positive dielectric anisotropy.

The F.E.M. cells account for a majority of liquid crystal display elements now in use. One important problem in the art is to make possible the low voltage operation of F.E.M. cells. In order to enable F.E.M. cells to be operated at low voltages, the threshold voltage of nematic liquid crystals to be filled in the cells should be minimized by adjusting the dielectric anisotropy of the nematic liquid crystals to a positive value above a certain point. For this purpose, compounds having a very high positive dielectric anisotropy are required as compounds for controlling dielectric constants. Addition of such compounds enables nematic liquid crystals having a negative dielectric anisotropy or a relatively low dielectric anisotropy to be applied to F.E.M. cells.

The compounds for controlling dielectric constants are required to have various properties. The following properties (a) to (e) are especially important.

(a) They should have a very large positive dielectric anisotropy.

(b) They should well dissolve in various nematic liquid crystals, should not crystallize at low temperatures, and should not increase the viscosities of nematic liquid crystals.

(c) They should not drastically narrow the liquid crystal temperature range of nematic liquid crystals, nor shift it to a higher temperature side.

(d) They should not markedly disorder the orderly molecular orientation of nematic liquid crystals.

(e) They should be chemically stable, and should not be decomposed by moisture, light, heat, etc.

Many compounds have been know to be effective for controlling dielectric constants. They include, for example, 4'-cyanophenyl 4-substituted benzoates (Japanese Patent Publication No. 2902/77), 4-substituted benzylideneamino-4'-cyanoanilines (Japanese Patent Publication No. 942/77), and 4,4'-disubstituted biphenyls (Japanese Laid-Open Patent Publication No. 95882/74). However, these known compounds have proved to be unsatisfactory in one or more of these properties (a) to (e).

It is an object of this invention therefore to provide novel dielectric controlling compounds having all of these properties (a) to (e).

According to this invention, this object can be achieved by 3'-chloro-4'-cyanophenyl 4-n-alkylbenzoates expressed by the general formula

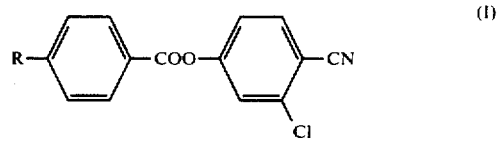

wherein R represents a linear alkyl group containing 1 to 9 carbon atoms.

In the course of the investigations of the present inventors which culminated in the discovery of the compounds of formula (I), they produced various compounds of a high positive dielectric anisotropy having the molecular structure of the type in which various polar substituents are introduced into the molecules of various nematic liquid crystals or the like, and carefully examined them for the aforesaid properties. However, these compounds have been found to possess poor solubility in nematic liquid crystals, or crystallize at low temperatures, or increase the viscosities of the nematic liquid crystals, or to markedly disorder the orderly molecular orientation of the nematic liquid crystals. Thus, these compounds have been found to be unacceptable in practical applications. In contrast, it is surprising that the compounds of formula (I) are free from the aforesaid defects, and possess all of the required properties (a) to (e).

According to this invention, the compounds of formula (I) can be produced by the following procedure.

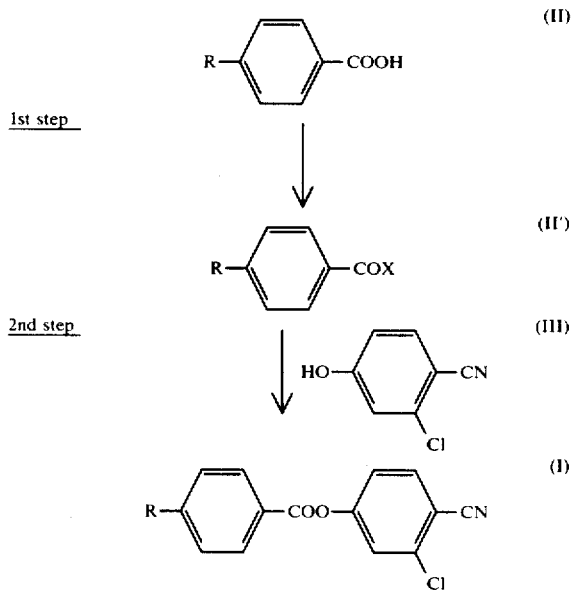

The first step comprises reacting the compound of formula (II)(wherein R is as defined) with a halogenating agent to produce the compound of formula (II')(wherein X is a halogen atom). In formula (II'), X is preferably a chlorine atom. Thionyl chloride can be used as the halogenating agent. The reaction is carried out under atmospheric pressure at the refluxing temperature of the reaction mixture. The mixture obtained by the reaction is submitted to the second-step reaction without isolating the compound of formula (II') but after only removing the excess of the halogenating agent.

The second step comprises reacting the crude compound of formula (II') obtained in the first step with the compound of formula (III) in an inert organic solvent. Examples of the inert organic solvent are diethyl ether, tetrahydrofuran, dimethylformamide and benzene. Desirably, a basic substance such as pyridine and tertiary amines is included in the inert organic solvent to remove the hydrogen halide freed during the reaction out of the reaction system. The reaction is carried out under atmospheric pressure at room temperature to the refluxing temperature of the reaction mixture. The compound of formula (I) can be isolated by subjecting the reaction product to a series of purifying treatments including solvent extraction, washing with water, drying, and recrystallization.

The compound of formula (III) as a raw material is produced by the following procedure.

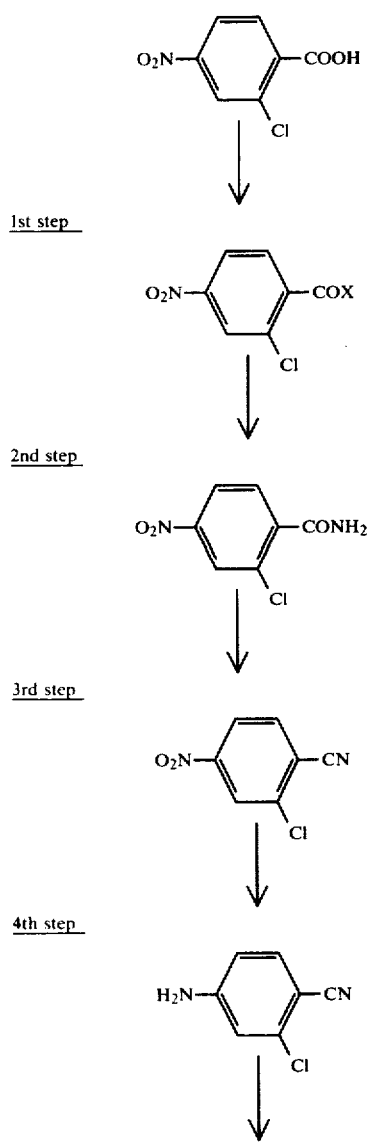

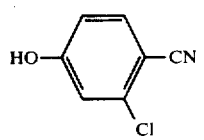

The first step comprises reacting the compound of formula (a) with a halogenating agent such as thionyl chloride, and distilling the reaction mixture to form the compound of formula (b) in which X is a halogen atom.

The second step comprises reacting the compound of formula (b) with ammonia solution at a temperature below room temperature, and washing the precipitated reaction mixture with water, followed by drying to afford the compound of formula (c).

The third step comprises reacting the compound of formula (c) with thionyl chloride under atmospheric pressure at the refluxing temperature, distilling off the thionyl chloride, extracting the reaction product with a solvent such as benzene, washing the extract with water, drying it, distilling off the extracting solvent from the extract, and recrystallizing the reaction product from methanol to afford the compound of formula (d).

The fourth step comprises reducing the compound of formula (d) with stannous chloride-conc. hydrochloric acid at room temperature, alkalizing the reaction mixture with an alkaline solution, extracting the reaction product with a solvent such as diethyl ether, washing the extract with water, distilling off the extracting solvent from the extract, and recrystallizing the resulting product from ethanol-water to afford the compound of formula (e).

The fifth step comprises adding the compound of formula (e) to an aqueous solution of sulfuric acid, adding an aqueous solution of sodium nitrite at a temperature of not more than 10° C. dropwise to the mixture to induce its reaction, removing the insoluble ingredients from the reaction mixture, adding a small amount of urea to the reaction mixture, reacting them at 70° to 75° C., separating the reaction product by filtration, and recrystallizing it from water to afford the compound of formula (III).

The physical properties of some compounds of formula (I) which are produced by the above procedure are tabulated below.

Table 1

| No. | R | m.p. (°C.) |
|---|---|---|
| (1) | $CH_3$ | 131 |
| (2) | $C_2H_5$ | 88 |
| (3) | $n-C_3H_7$ | 63 |
| (4) | $n-C_4H_9$ | 34 |
| (5) | $n-C_5H_{11}$ | 35 |
| (6) | $n-C_6H_{13}$ | 38 |
| (7) | $n-C_7H_{15}$ | 32 |
| (8) | $n-C_8H_{17}$ | 31 |
| (9) | $n-C_9H_{19}$ | 29 |

The compounds of formula (I) act effectively as dielectric controlling compounds on all nematic liquid crystals, and therefore can be used in combination with any type of nematic liquid crystals. For example, compositions obtained by mixing nematic liquid crystals such as a phenyl 4,4'-disubstituted benzoate, thiophenyl 4,4'-disubstituted benzoate, 4,4'-disubstituted benzylidene aniline, 4,4'-disubstituted azoxybenzene, 4,4'-disubstituted biphenyl, phenyl 4,4'-disubstituted cyclohexanecarboxylate, 4,4'-disubstituted phenylcyclohexane, or 4,4'-disubstituted biphenylcyclohexane with the compounds of formula (I) are preferred liquid crystalline compositions for F.E.M. cells. The proportion of the compound of formula (I) is not restricted in particular. Generally, the suitable proportion is 5 to 30 mole% based on the total amount of the nematic liquid crystals and the compound of formula (I).

Table 2 summarizes the physical and electro-optical properties of some examples of nematic liquid crystalline compositions consisting of (A) 90 mole% of a nematic liquid crystalline compound consisting of 65 mole% of

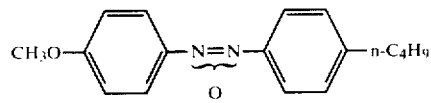

and 35 mole% of

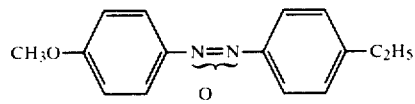

and (B) 10 mole% of each of the compounds (1) to (9) shown in Table 1 [compounds of formula (I)].

In the column of Transition temperature in the table, C represents a solid phase; N, a nematic liquid crystalline phase; and I, an isotropic liquid phase. The threshold voltage is measured by using a liquid crystal cell obtained by filling the sample into an F.E.M. cell adapted to contain the liquid crystals as a 10 μm-thick layer. A variable voltage of 1 KHz sine waves is applied to the liquid crystal cell, and the threshold voltage is defined at the voltage at which the amount of light transmitted reaches 90%. The standards of the amount of light transmitted (%) are that the amount of light transmitted in the absence of the application of voltage is taken as 100%, and the amount of light transmitted when the light of a light source is completely shielded is taken as 0%.

Table 2

| | Transition temperature (°C.) | | Threshold voltage |
|---|---|---|---|
| | C · N | N · I | (volts, 25° C.) |
| Liquid crystalline compound (A) | −5 | 75 | — |
| (A) + (1) | Precipitated at room temperature | 59 | 1.80 (40° C.) |
| (A) + (2) | −5 | 59 | 1.85 |
| (A) + (3) | −7 | 60.5 | 1.90 |
| (A) + (4) | −8 | 61 | 1.90 |
| (A) + (5) | 8 | 62 | 1.90 |
| (A) + (6) | 9 | 61 | 1.90 |
| (A) + (7) | 9 | 63.5 | 1.95 |
| (A) + (8) | 9 | 58 | 2.0 |
| (A) + (9) | 12 | 59 | 1.0 |

The nematic liquid crystalline compound (A) alone is inapplicable to F.E.M. cells because it has a negative dielectric anisotropy. As is clearly seen from the data shown in Table 2, the inclusion of a small amount of the compound of formula (I) enables this nematic liquid crystalline compound (A) to be applied to F.E.M. cells, and the threshold voltages of the resulting nematic liquid crystalline compositions decrease very much.

For comparison, a compound of the formula

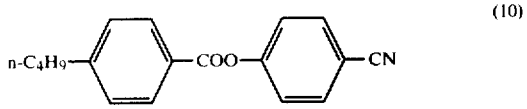

(10)

was chosen as a typical prior art compound capable of rendering nematic liquid crystals applicable to F.E.M. cells, and was mixed in varying amounts with the nematic liquid crystalline compound (A) described hereinabove. Likewise, the compound (4) of formula (I) in accordance with this invention which has the following formula

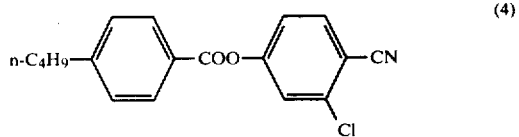

(4)

was mixed in varying amounts with the nematic liquid crystalline compound (A). The threshold voltages of the resulting nematic liquid crystalline compositions were measured. The results of measurements were plotted in the accompanying drawing.

Substantially the same graphs as in the case of compound (4) were obtained with the compounds (1) to (3) and (5) to (9) of this invention.

It can be understood from the above fact that the compounds of this invention can reduce the threshold voltages of nematic liquid crystals to a far greater extent than the typical prior art compound.

The following Material Production Example and Examples illustrate the present invention more specifically.

MATERIAL PRODUCTION EXAMPLE (1) Thionyl chloride (1,200 g) was added to 500 g (2.48 moles) of the compound

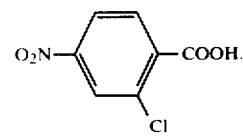

The mixture was reacted for 2 hours under reflux, and the excess of the thionyl chloride was distilled off. Vacuum distillation of the resulting product afforded 484 g of the compound

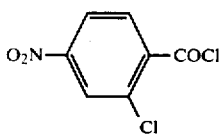

having a boiling point of 143° C./4 mmHg.

(2) Two thousand grams of 29% ammonia solution was cooled to 10°–15° C., and with vigorous stirring, 484 g of the compound

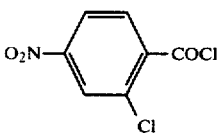

was added dropwise. After the addition, the resulting precipitate was collected by filtration, washed with water and 30% methanol solution, and dried in vacuum to afford 416 g of the compound

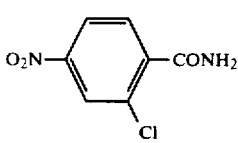

having a melting point of 168°–172° C.

(3) Thionyl chloride (2,000 g) was added to 416 g of the compound

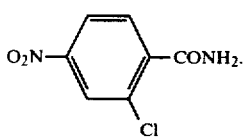

The mixture was reacted for 3 hours under reflux, and the excess of the thionyl chloride was distilled off. The reaction mixture was cooled, and water was added. Then, the reaction product was extracted with benzene. The extract was washed with a 2% aqueous solution of sodium hydroxide, further washed with water until it became neutral, and then dried over anhydrous sodium sulfate. The benzene was then distilled off from the extract, and the reaction product was recrystallized from methanol to afford 318 g of the compound

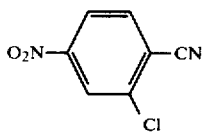

having a melting point of 75° C.

(4) Stannous chloride (1,300 g) was dissolved in 1,300 cc of conc. hydrochloric acid, and the solution was cooled. With stirring, 318 g of the compound

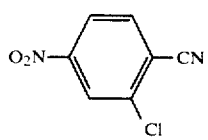

was added slowly to the solution. The solution was then maintained at 25° to 35° C. for 5 hours. Then, while being cooled, the reaction mixture was alkalized with a 20% aqueous solution of sodium hydroxide. The reaction mixture was fully stirred, and the reaction product was extracted with diethyl ether. The reaction product was recrystallized from 50% ethanol solution to afford 228 g of the compound

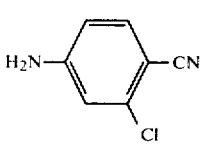

having a melting point of 117° C.

(5) Conc. sulfuric acid (93%; 463 g) was dissolved in 4,500 cc of water, and the solution was cooled. Then, 228 g of the compound

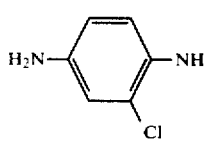

was added to the solution, and the mixture was stirred for 1 hour. Then, the mixture was maintained at 5° to 7° C., and a solution of 106 g of 97% sodium nitrite in 1,000 cc of water was added dropwise. After the addition, they were reacted for 2 hours. The water-insoluble matter was removed from the reaction mixture, and 12 g of urea was added. The mixture was then reacted at 70° to 75° C. for 3 hours. The reaction mixture was cooled, and the resulting precipitate was collected by filtration. It was recrystallized from water to afford 148 g of a compound of the following formula. The yield of this compound through the entire reaction steps (1) to (5) was 38.9%.

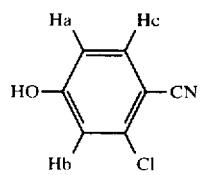

m.p. 158° C.
NMR [in $(CD_3)_2CO$]
$\delta$(PPM):
 6.88 (d, 1H, Ha)
 7.04 (dd, 1H, Hb)
 7.63 (d, 1H, Hc)
 >9.0 (s, 1H, —OH).

EXAMPLE 1

Thionyl chloride (100 cc) was added to 13.6 g (0.100 mole) of the compound

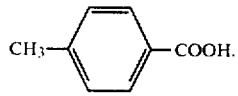

The mixture was reacted for 30 minutes under reflux, and then the excess of the thionyl chloride was distilled off. To the reaction product were added 15.4 g (0.100 mole) of the compound

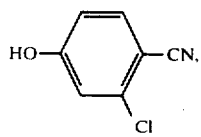

150 cc of diethyl ether and 11 g of pyridine. They were reacted for 2 hours at room temperature with stirring. The reaction mixture was washed with 1% hydrochloric acid and water to render it neutral. Then, the diethyl ether was distilled off from the reaction mixture. Recrystallization of the reaction product from methanol afforded 21.5 g (0.00792 mole) of a compound of the following formula in a yield of 79.2%.

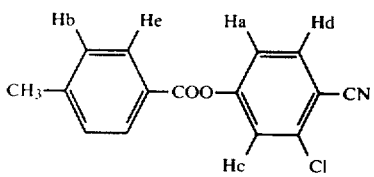

NMR (in CDCl$_4$)
δ(PPM):
2.42 (s, 3H, —CH$_3$)
7.2–7.4 (dd, d, 1H, 2H, Ha, Hb)
7.41 (d, 1H, Hc)
7.67 (d, 1H, Hd)
8.03 (d, 2H, He).

EXAMPLE 2

Example 1 was repeated except that 0.100 mole each of the compounds shown in Table 3 was used instead of 0.100 mole of the compound

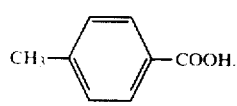

In Table 3, the asterisk (*) shows two broad peaks.

Table 3

| R | Yield (%) | NMR (in CDCl$_4$) |
|---|---|---|
| C$_2$H$_5$ | 74.1 | δ(PPM): 1.29 (t, 3H, —CH$_3$); 2.74 (q, 2H, —CH$_2$—); 7.2–7.7 (dd, d, 1H, 2H, Ha, Hb); 7.43 (d, 1H, Hc); 7.68 (d, 1H, Hd); 8.07 (d, 2H, He) |
| n-C$_3$H$_7$ | 76.3 | δ(PPM): 0.96 (t, 3H, —CH$_3$); 1.1–1.8 (m, 2H, —C—CH$_2$—C—); 2.75 (t, 2H, —CH$_2$—Ph); 7.2–7.4 (dd, d, 1H, 2H, Ha, Hb); 7.43 (d, 1H, Hc); 7.68 (d, 1H, Hd); 8.07 (d, 2H, He) |
| n-C$_4$H$_9$ | 72.6 | δ(PPM): 0.94 (t, 3H, —CH$_3$); 1.1–1.8 (m, 4H, —C—(CH$_2$)$_2$—C—); 2.72 (t, 2H, —CH$_2$—Ph); 7.2–7.4 (dd, d, 1H, 2H, Ha, Hb); 7.43 (d, 1H, Hc); 7.68 (d, 1H, Hd); 8.07 (d, 2H, He) |
| n-C$_5$H$_{11}$ | 73.0 | δ(PPM): 0.92 (t, 3H, —CH$_3$); 1.1–1.8 (m, 6H, —C—(CH$_2$)$_3$—C—); 2.70 (t, 3H, —CH$_2$—Ph); 7.2–7.4 (dd, d, 1H, 2H, Ha, Hb); 7.43 (d, 1H, Hc); 7.68 (d, 1H, Hd); 8.07 (d, 2H, He) |
| n-C$_6$H$_{13}$ | 70.8 | δ(PPM): 0.90 (t, 3H, —CH$_3$); 1.0–1.8 (*, 8H, —C—(CH$_2$)$_4$—C—); 2.67 (t, 2H, —CH$_2$—Ph); 7.2–7.4 (dd, d, 1H, 2H, Ha, Hb); 7.43 (d, 1H, Hc); 7.66 (d, 1H, Hd); 8.04 (d, 2H, He) |
| n-C$_7$H$_{15}$ | 71.5 | δ(PPM): 0.88 (t, 3H, —CH$_3$); 1.0–1.8 (*, 10H, —C—(CH$_2$)$_5$—C—); 2.67 (t, 2H, —CH$_2$—Ph); 7.2–7.4 (dd, d, 1H, 2H, Ha, Hb); 7.43 (d, 1H, Hc); 7.66 (d, 1H, Hd); 8.05 (d, 2H, He) |
| n-C$_8$H$_{17}$ | 69.4 | δ(PPM): 0.88 (t, 3H, —CH$_3$); 1.0–1.8 (*, 12H, —C—(CH$_2$)$_6$—C—); 2.70 (t, 2H, —CH$_2$—Ph) |

Table 3-continued

| R | Yield (%) | NMR (in CDCl4) |
|---|---|---|
| | | 7.2–7.4 (dd, d, 1H, 2H, Ha, Hb) |
| | | 7.43 (d, 1H, Hc) |
| | | 7.68 (d, 1H, Hd) |
| | | 8.05 (d, 2H, He) |
| | | δ(PPM): |
| n-C9H19 | 68.8 | 0.88 (t, 3H, —CH3) |
| | | 1.0–1.8 (*, 14H, —C—(CH2)7—C—) |
| | | 2.70 (t, 2H, —CH2—Ph) |
| | | 7.2–7.4 (dd, d, 1H, 2H, Ha, Hb) |
| | | 7.42 (d, 1H, Hc) |
| | | 7.69 (d, 1H, Hd) |
| | | 8.05 (d, 2H, He) |

What we claim is:

1. A compound of the general formula

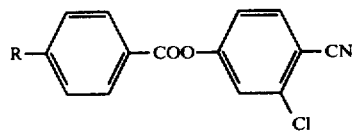

wherein R represents a linear alkyl group containing 1 to 9 carbon atoms.

2. The compound of claim 1 which has the formula

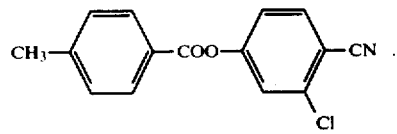

3. The compound of claim 1 which has the formula

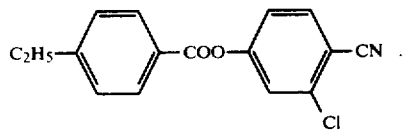

4. The compound of claim 1 which has the formula

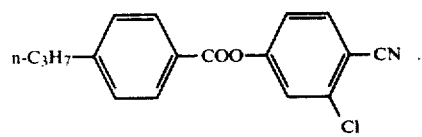

5. The compound of claim 1 which has the formula

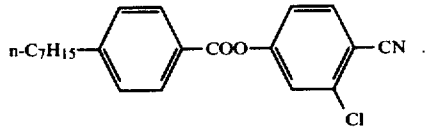

6. The compound of claim 1 which has the formula

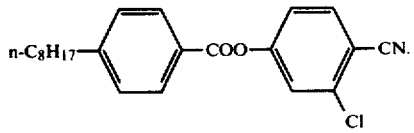

7. The compound of claim 1 which has the formula

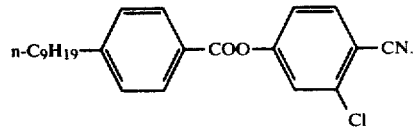

8. The compound of claim 1 which has the formula

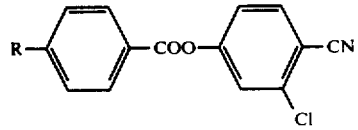

9. The compound of claim 1 which has the formula

10. The compound of claim 1 which has the formula

11. A nematic liquid crystalline composition comprising (1) at least one nematic liquid crystal and (2) from 5 to 30 mole percent, based on the total weight of the nematic liquid crystal, of a compound of formula (I)

wherein R represents a linear alkyl group containing 1 to 9 carbon atoms, said composition having a positive dielectric anisotropy suitable for use in a field effect mode liquid crystal display cell.

12. The composition of claim 11 wherein the nematic liquid crystal is at least one member selected from the group consisting of phenyl 4,4'-disubstituted benzoate, thiophenyl 4,4'-disubstituted benzoate, 4,4'-disubstituted benzylidene aniline, 4,4'-disubstituted azoxybenzene, 4,4'-disubstituted biphenyl, phenyl 4,4'-disubstituted cyclohexanecarboxylate, 4,4'-disubstituted phenylcyclohexane, and 4,4'-disubstituted biphenylcyclohexane.

13. The composition of claim 11 which comprises (A) 90 mole% of a nematic liquid crystalline compound consisting of 65 mole% of

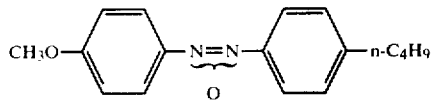

and 35 mole% of

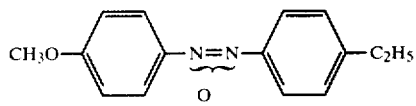

and (B) 10 mole% of one of the compounds of formula (I).

* * * * *